(12) United States Patent
Ruiter

(10) Patent No.: US 7,998,082 B2
(45) Date of Patent: Aug. 16, 2011

(54) THERMO-DILUTION CARDIAC OUTPUT MEASUREMENT SIMULATOR

(75) Inventor: Karl A. Ruiter, Honolulu, HI (US)

(73) Assignee: Pronk Technologies, Inc., Sun Valley, CA (US)

( * ) Notice: Subject to any disclaimer, the term of this patent is extended or adjusted under 35 U.S.C. 154(b) by 370 days.

(21) Appl. No.: 12/203,586

(22) Filed: Sep. 3, 2008

(65) Prior Publication Data

US 2009/0069705 A1   Mar. 12, 2009

Related U.S. Application Data

(60) Provisional application No. 60/970,662, filed on Sep. 7, 2007.

(51) Int. Cl.
*A61B 5/028* (2006.01)
(52) U.S. Cl. ........................................... 600/508
(58) Field of Classification Search .............. 600/526; 60/508–528
See application file for complete search history.

(56) References Cited

U.S. PATENT DOCUMENTS 5,526,817 A    6/1996   Pfeiffer et al.
2003/0187362 A1*  10/2003   Murphy et al. ............... 600/508

FOREIGN PATENT DOCUMENTS

EP           0 596 539 A2     5/1994

OTHER PUBLICATIONS

PCT/US08/075132, Mar. 11, 2009, Pronk Technologies, Inc., international Search Report.
Kinder, Bernadette and Purves, Robert, "The 'Cardiac Output' Chart extension," Application Note, AEM30A, ADInstruments Pty Ltd., Nov. 2000, pp. 1-2.
Nadeau, Sophie and Noble, William H.,"Limitations of cardiac output measurements by thermodilution," Canadian Anaesthetist's Society Journal, 1986, vol. 33, No. 6,pp. 780-784.

* cited by examiner

*Primary Examiner* — Scott M Getzow
*Assistant Examiner* — Amanda Patton
(74) *Attorney, Agent, or Firm* — Michael Blaine Brooks, PC; Michael B. Brooks

(57) ABSTRACT

The present invention includes machine-enabled methods of, and devices and systems for, simulating thermo-dilution cardiac output measurements based on ambient room temperature measurements via the injectate temperature sensor.

4 Claims, 3 Drawing Sheets

THERMO-DILUTION CARDIAC OUTPUT MEASUREMENT SIMULATOR

CROSS-REFERENCE TO RELATED APPLICATION

This application claims the benefit of U.S. Provisional Patent Application Ser. No. 60/970,662 filed Sep. 7, 2007, which is hereby incorporated by reference herein for all purposes.

FIELD OF ENDEAVOR

The present invention relates to the field of hemodynamic monitoring in humans and animals, specifically the simulation of thermo-dilution cardiac output measurement.

BACKGROUND

Cardiac output may be measured using a thermo-dilution technique where a fluid, such as chilled water may be injected into the blood stream and the measured temperature decay rate, i.e., the warming in the local area of injection over time, is used to indicate or infer cardiac volumetric output. The injectate temperature and volume provide an initial condition for a process of a homeothermic organism that may be simulated. That is, as the temperature of the blood fluid proximate to the injection point rises over a period of time toward the expected homeothermic level, one may infer the blood volume flow causing the measured temperature increase.

FIG. 1 illustrates a setup or system for measuring cardiac output using a thermo-dilution technique. A catheter 100 is inserted into an artery 101 of a human patient's flesh 102, e.g., into an artery of a person's upper arm. At the distal end of the catheter or a lumen within, or extending from, the catheter is shown with a thermistor 103 for measuring blood temperature. To initiate a thermo-dilution cardiac output measurement process, cold fluid is injected into the artery through the catheter via a syringe 104. The temperature of the injected fluid is measured by an injectate temperature thermistor 105. Both the blood temperature thermistor and the injectate temperature thermistor make electrical connections to a cardiac output computer 106 via electrical connectors 107, 108 and cables 127, 128. A cardiac output computer 106 may include a central processing unit (CPU), addressable memory, a display 109, and an input panel 110.

For training and testing purposes it is often useful to simulate a cardiac output measurement and provide a display of a representative value of cardiac output. Simulators may simulate both the blood temperature and injectate temperature thermistors. The thermistors 103 used for blood temperature sensing in FIG. 1 typically have standard electrical properties and typically use a standard electrical connection 107, however the thermistors used for injectate temperature sensing may not have standard electrical properties and/or may not use a standard connection. Accordingly, cardiac output simulators generally may be in electrical communication via vendor-specific adapter cables which comprise one or more vendor-specific fixed resistance values to simulate injectate temperature and the vendor-specific injectate temperature connector. The vendor-specific adapter cables are typically relatively expensive and bulky.

SUMMARY

The present invention includes machine-enabled methods of, and devices and systems for, simulating thermo-dilution cardiac output measurement based on ambient room temperature measurements via the injectate temperature sensor. An exemplary machine-enabled method comprises: (a) measuring ambient room temperature; (b) determining a cardiac output estimate coefficient correction based on the measured ambient room temperature as a simulated injectate temperature; (c) determining a cardiac output estimate based on the determined cardiac output estimate coefficient correction; and (d) outputting the determined cardiac output estimate as a simulated thermo-dilution cardiac output measurement. Some embodiments of the machine-enabled method may have a step of determining the cardiac output estimate coefficient correction that is further based on a simulated blood temperature and a nominal injectate volume.

Device and system embodiments of the present invention include a thermo-dilution cardiac output measurement simulator comprising: a central processing unit and addressable memory, where the central processing unit may be configured to: (a) receive a measurement of ambient room temperature; (b) determine a cardiac output estimate coefficient correction based on the measured ambient room temperature as a simulated injectate temperature; (c) determine a cardiac output estimate based on the determined cardiac output estimate coefficient correction; and (d) output the determined cardiac output estimate as a simulated thermo-dilution cardiac output measurement. Some embodiments of the thermo-dilution cardiac output measurement simulator may have a central processing unit that is further configured to determine the cardiac output estimate coefficient correction based on a simulated blood temperature and a nominal injectate volume.

BRIEF DESCRIPTION OF THE DRAWINGS

Embodiments of the present invention are illustrated by way of example and not limitation in the figures of the accompanying drawings, and in which.

DETAILED DESCRIPTION

A cardiac output estimate may be determined by referencing the time profile of a temporary drop in blood stream temperature caused by the introduction of colder injectate into the blood stream. The method of cardiac output value determination or estimation may be based on the Stewart-Hamilton formula. For example, for cardiac output (C.O.):

$$C.O. = V_i * (T_b - T_i) * K / \int \Delta T \, dt;$$

where, in the above equation, the volume of the injection is represented by $V_i$, the blood temperature is represented by $T_b$, the injectate temperature is represented by $T_i$, the change in blood temperature over time is represented by $\Delta T$, time is represented by t, and a correlation factor is represented by K.

The method of cardiac output value determination or estimation may be further based on a computation coefficient, CC, which may be applied, for example as a gain or multiplier to K, in order to correct the determined or estimated cardiac output for factors; factors such as specific thermistor characteristics, particularly addressing characteristics of a thermistor disposed in the tip or proximate to the distal tip of the catheter and factors such as varying injectate volumes.

Figure 1:
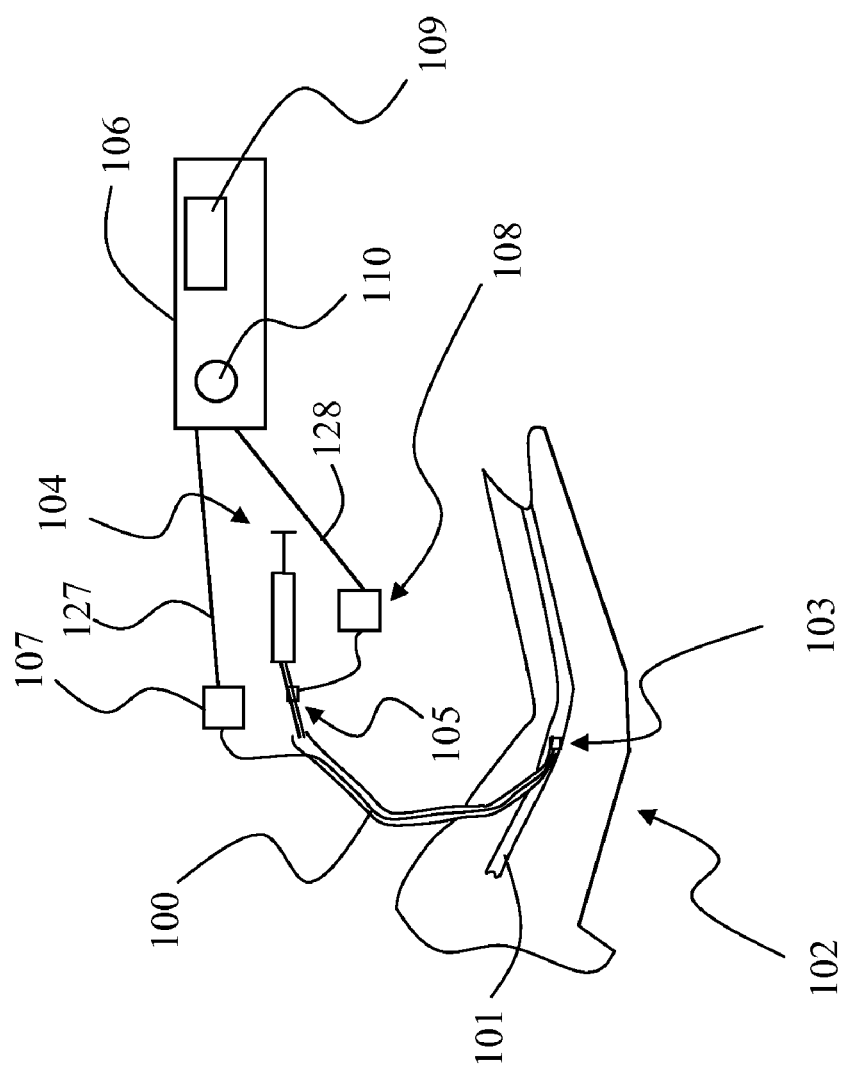
FIG. 1 is prior art system for measuring cardiac output using a thermo-dilution technique.
Figure 2:
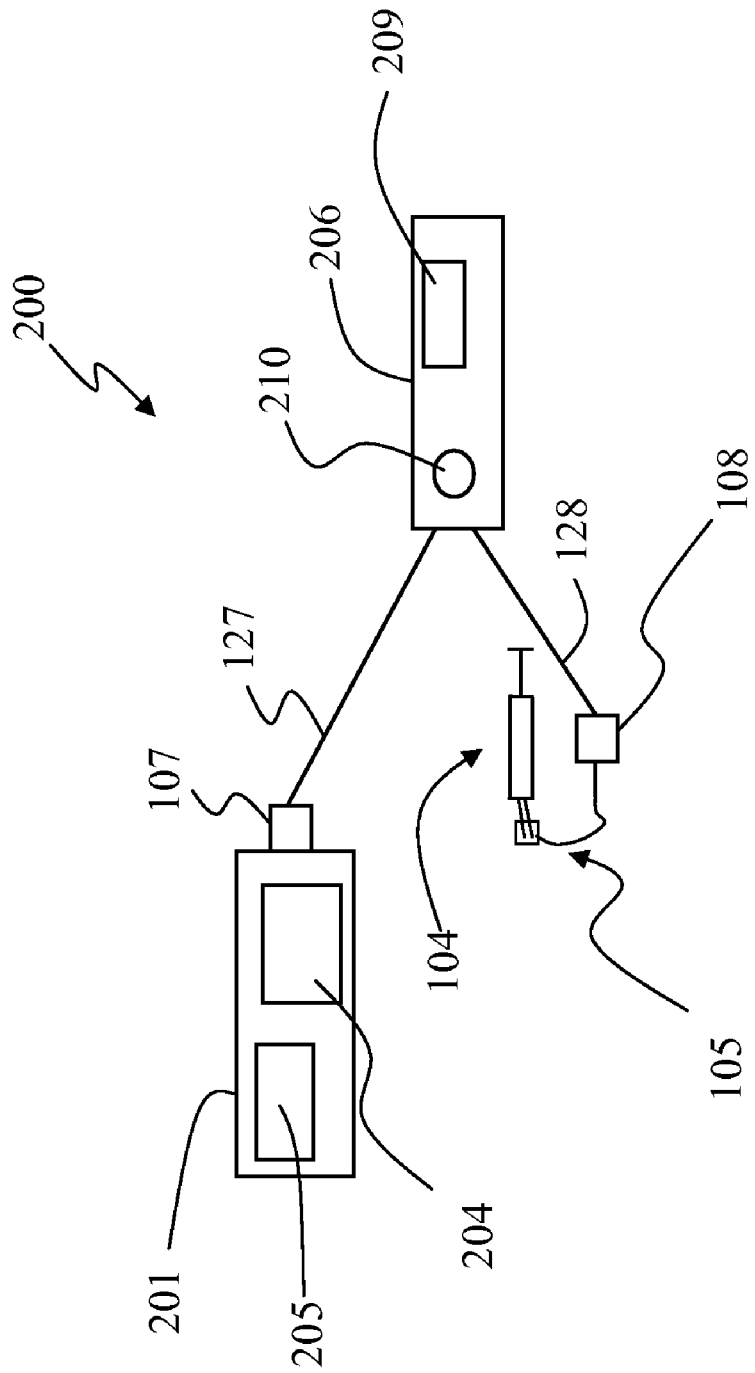
FIG. 2 is a functional diagram of a system/device embodiment of the present invention.

FIG. 2 shows an embodiment of the present invention 200 using typical cables. A cardiac output simulator embodiment of the present invention is configured to electrically interface with an electrical connector 107. The exemplary cardiac output simulator also includes a central processing unit, e.g., a microprocessor, addressable memory and a user interface 204. The cardiac output computer 206, in this example, is connected directly to the cardiac output simulator 201 embodiment of the present invention via a typical blood temperature thermistor cable 127 and connector 107. The cardiac output computer 206 is also connected, in this example, to a typical injectate temperature sensor, e.g., thermistor 105 via a typical cable 128 and connector 108. Some embodiments of the cardiac output computer 206, particularly those not including a touch screen display, may further comprise a tactile interface 210 comprised of buttons and/or switches.

The main body of an exemplary cardiac output simulator 201 of the present invention generally comprises an electronically variable resistance that is typically under microprocessor control for simulating the standard blood temperature thermistor's curve during an injection cycle, as well as the standard blood temperature thermistor interface connector, and also comprises a user interface which allows for simulated injections to be initiated and for simulated cardiac output values to be selected. The cardiac output computer 206 may be configured to receive and process, as measurements of injectate temperature, the electrical signals from the injectate temperature thermistor 105 via an electrical connector 108 and cable 128 and to receive and process, as measurements of blood temperature, the electrical signals from the catheter-borne thermistor 103 via an electrical connector 107 and a cable 127. An LED or LCD display or other display 209 may be used as a portion of a user interface, a graphic user interface, or as a means for displaying blood temperature and injectate temperature to a user. In addition, the cardiac output computer processor may be configured to determine a value representative of cardiac output and that value may be displayed as a volume rate of blood flow, e.g., in liters per minute. Some embodiments of the cardiac output computer 106, particularly those embodiments not including a touch screen display, may further comprise a tactile interface 110 comprised of buttons and/or switches.

The exemplary cardiac output simulator 201 comprises an electronically variable resistance under microprocessor control for simulating the standard blood temperature thermistor's output curve over time, i.e., during the time interval of an injection cycle, as well as, the standard blood temperature thermistor interface connector 107, and further comprises a user interface 204 which allows simulated injections to be initiated and simulated cardiac output values to be selected. The processor of the cardiac output computer 206 may be configured to fetch or input a corrected computation coefficient based on the ambient or room temperature measured by the typical injectate thermistor 105. In some embodiments, the computation coefficient (CC) may be generated by the processing at the cardiac output computer or via the processing at the cardiac output simulator 201. That is, the computer processor of the device may be configured to generate a CC for use in a cardiac output determination and the generated CC may be inversely based on the measured injectate temperature, $T_i$, for example, $CC=6/(37.0-T_i)$.

In an exemplary method of use of the exemplary embodiment of the present invention, the normal injectate temperature thermistor 105 is disposed to measure room temperature. The processor of the cardiac output simulator 201 may be further configured to determine the correction coefficient (CC) value based on the measured injectate temperature. In another embodiment, the processor of the cardiac output simulator 201 is configured to fetch or input the value of the displayed injectate temperature via a user interface 204 and output, e.g., via a display, a derived correction coefficient to be input into the cardiac output computer 206 via a communication link or by the user. In another embodiment, the processor of the cardiac output simulator 201 may be further configured to determine the correction coefficient (CC) value based on the measured injectate temperature. In another embodiment, the measurement of the injectate temperature thermistor 105 may be displayed to a user via the display 209 of the cardiac output computer 206. A user may read the displayed injectate temperature and either perform a calculation or draw the value from a reference table 205 of pre-calculated values representative of appropriate correction coefficients presented as a function of the displayed injectate temperature. In another embodiment, the processor of the cardiac output simulator 201 is configured to fetch or input the value of the displayed injectate temperature via a user interface 204 and output, e.g., via a display, a derived correction coefficient to be input into the cardiac output computer 206 via a communication link or by the user. In another embodiment, the processor of the cardiac output simulator 201 may be further configured to determine the correction coefficient (CC) value based on the measured injectate temperature.

In some embodiments, the CC is generated by the processing at the cardiac output computer or via the processing at the cardiac output simulator 201. For example, once the ambient temperature is measured and processed as the injectate temperature, $T_i$, a CC may be determined, e.g., $CC=6/(37.0-T_i)$, and the CC may be applied in determining an estimate of the cardiac output for simulation purposes. Accordingly, the cardiac output computer 206 processing, or the cardiac output simulator 201 processing, may be configured to output a value for cardiac output based on a modified Stewart-Hamilton formula incorporating the CC. For example, $$\text{Cardiac Output } (C.O.): C.O.=CC*V_i*(T_b-T_i)*K/\int\Delta T\,dt].$$

In another exemplary embodiment, the simulated blood temperature thermistor curve is applied such that with an injectate temperature of 25.0 degrees C., a computation coefficient, CC, of 0.500 will produce cardiac output calculations on the cardiac output computer 206 which match the selected value of the simulator.

For some exemplary embodiments, associated documentation may generally instruct a user of the simulator to enter a single specific calculation coefficient into the cardiac output computer and in particular may include a table that represents the equation $CC=6/(37.0-T_i)$, where CC is the computation coefficient to be entered into the cardiac output computer 206, and $T_i$ is the value of the room temperature read via the cardiac output computer's injectate temperature sensor 105, in degrees C. (in this example). In some embodiments, the table of computation coefficients 205, i.e., CC based on ambient injectate temperature, that may be printed on the device may be replaced by a similar table printed in a manual, a formula printed on the device or in the manual, or a function of the cardiac output simulator 201 which calculates and displays the computation coefficient on an electronic display based on a user input of injectate temperature or by the cardiac output computer 206.

A method embodiment of simulating thermo-dilution cardiac output measurement may include: (a) attaching the blood temperature port of a cardiac output computer to a thermo-dilution blood temperature simulator; (b) attaching the injectate temperature port of said cardiac output computer to a thermistor; (c) reading the indicated injectate temperature value from said cardiac output computer; (d) determining a corrected cardiac output calculation coefficient based on the indicated injectate temperature, (e) if the determining of the corrected cardiac output calculation coefficient was not done by the cardiac output computer, then entering into, or communicating the corrected cardiac output calculation coefficient to, the cardiac output computer; and (f) initiating a thermo-dilution blood temperature simulation on said thermo-dilution blood temperature simulator. The method may have the corrected cardiac output calculation coefficient determined according to $CC=6(37-T_i)$ where CC is the corrected cardiac output calculation coefficient and $T_i$ is the injectate temperature in Celsius. The method may have the calculation facilitated by a table of corrected cardiac output coefficient values, indexed by injectate temperature values which may be printed on the thermo-dilution blood temperature simulator. In some embodiments, the method may have the calculation facilitated by a table of corrected cardiac output coefficient values, indexed by injectated temperature values, which may be printed in the user manual of the thermo-dilution blood temperature simulator.

In other embodiments, the method may be facilated by electronic functions of the thermo-dilution blood temperature simulator by which a user may input the injectate temperature and where the blood temperature simulator electronically calculates and displays the corrected cardiac output coefficient value. In some embodiments, the corrected cardiac output calculation coefficient may be determined according to $CC=K_1(K_2-T_i)$ where CC is the corrected cardiac output calculation coefficient, $T_i$ is the injectate temperature, $K_2$ is the simulated blood temperature, and $K_1$ is given by $K_1=(K_2-$ nominal injectate temperature)/nominal CC value, where the nominal injectate temperature is the central, typical, or usual value for the injectate temperature value, and where the nominal CC value is an expected or convenient value for the cardiac output coefficient value.

Figure 3:
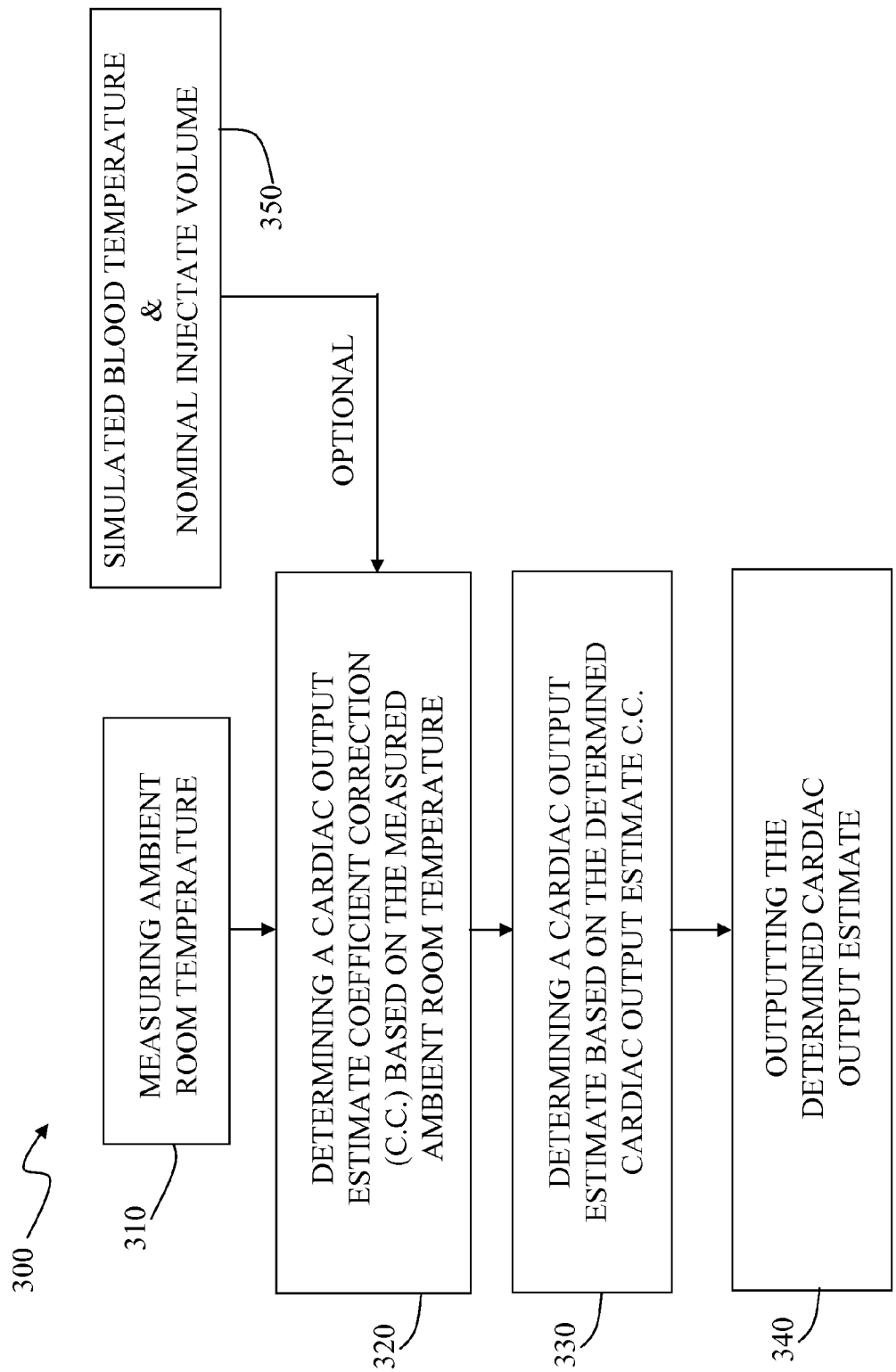
FIG. 3 is a flowchart of a process embodiment of the present invention.

FIG. 3 illustrates in a top level block diagram process steps 300 of a device, machine or system embodiment of the present invention. The ambient room temperature is measured (step 310). A cardiac output estimate CC is determined (step 320) based on the measured room temperature, for example, via the injectate temperature sensor. A cardiac output estimate is determined (step 330) based on the CC. The determined cardiac output estimate is output (step 340) via a display, print out, or combinations thereof. As an option (block 350), the step of determining the cardiac output CC (step 320) may be based on simulated blood temperature and a nominal injectate volume.

Many alterations and modifications may be made by those having ordinary skill in the art without departing from the spirit and scope of the invention. Therefore, it must be understood that the illustrated embodiments have been set forth only for the purposes of example and that it should not be taken as limiting the invention as defined by the following claims.

What is claimed is:

1. A machine-enabled method of simulating thermo-dilution cardiac output measurement comprising:
   measuring ambient room temperature;
   determining a cardiac output estimate coefficient correction wherein the measured ambient room temperature is a simulated injectate temperature; and
   determining a cardiac output estimate as a simulated thermo-dilution cardiac output measurement based on the determined cardiac output estimate coefficient correction.

2. The machine-enabled method of claim 1 wherein the step of determining the cardiac output estimate coefficient correction is further based on a simulated blood temperature and a nominal injectate volume.

3. A thermo-dilution cardiac output measurement simulator comprising:
   a central processing unit and addressable memory;
   wherein the central processing unit is configured to:
      receive a measurement of ambient room temperature;
      determine a cardiac output estimate coefficient correction wherein the measured ambient room temperature is a simulated injectate temperature; and
      determine a cardiac output estimate as a simulated thermo-dilution cardiac output measurement based on the determined cardiac output estimate coefficient correction.

4. The thermo-dilution cardiac output measurement simulator of claim 3 wherein the central processing unit is further configured to determine the cardiac output estimate coefficient correction based on a simulated blood temperature and a nominal injectate volume.

* * * * *